US009982090B2

(12) United States Patent
Choi et al.

(10) Patent No.: US 9,982,090 B2
(45) Date of Patent: May 29, 2018

(54) METHOD FOR MANUFACTURING POLYDIOXANONE PARTICLES FOR FILLER

(71) Applicant: ULTRA V CO., LTD., Incheon (KR)

(72) Inventors: Myung Choi, Seoul (KR); Sang Jin Kim, Busan (KR); Byeung Mo Chang, Seoul (KR); Michael Gilbert Douglas, Georgetown, TX (US); Han Jin Kwon, Seoul (KR)

(73) Assignee: ULTRA V CO., LTD., Incheon (KR)

( * ) Notice: Subject to any disclaimer, the term of this patent is extended or adjusted under 35 U.S.C. 154(b) by 0 days. days.

(21) Appl. No.: 15/308,291

(22) PCT Filed: Jul. 16, 2015

(86) PCT No.: PCT/KR2015/007414
§ 371 (c)(1),
(2) Date: Nov. 1, 2016

(87) PCT Pub. No.: WO2016/010388
PCT Pub. Date: Jan. 21, 2016

(65) Prior Publication Data
US 2017/0129993 A1    May 11, 2017

(30) Foreign Application Priority Data
Jul. 17, 2014  (KR) .................. 10-2014-0090590

(51) Int. Cl.
*C08G 63/664* (2006.01)
*C08G 63/90* (2006.01)
*A61L 27/18* (2006.01)

(52) U.S. Cl.
CPC ............ *C08G 63/664* (2013.01); *A61L 27/18* (2013.01); *C08G 63/90* (2013.01); *A61L 2400/06* (2013.01); *A61L 2430/34* (2013.01); *C08G 2230/00* (2013.01)

(58) Field of Classification Search
CPC ....... A61K 9/10; A61L 31/146; C08G 63/664; C08G 63/90
See application file for complete search history.

(56) References Cited

U.S. PATENT DOCUMENTS

| | | |
|---|---|---|
| 4,017,670 A | 4/1977 | Spicuzza, Jr. et al. |
| 4,071,670 A | 1/1978 | Vanzo et al. |
| 4,085,169 A | 4/1978 | Saito et al. |
| 4,129,706 A | 12/1978 | Keppler et al. |
| 5,852,140 A | 12/1998 | Georges et al. |
| 2009/0317478 A1* | 12/2009 | Han .................. A61K 9/1647 424/497 |
| 2013/0045266 A1* | 2/2013 | Choi .................. A61K 9/5031 424/422 |
| 2013/0316006 A1* | 11/2013 | Popov .................. A61K 9/5015 424/491 |

FOREIGN PATENT DOCUMENTS

| | | |
|---|---|---|
| CN | 1149596 A | 5/1997 |
| CN | 1361684 A | 7/2002 |
| EP | 0443609 B2 | 8/1991 |
| JP | 11-060615 A | 3/1999 |
| KR | 10-2002-0008815 A | 1/2002 |
| KR | 10-2007-0018008 A | 2/2007 |
| KR | 10-2009-0129669 A | 12/2009 |
| KR | 10-2010-0104219 A | 9/2010 |
| KR | 10-2011-0075618 A | 7/2011 |
| WO | 1999/019370 A1 | 4/1999 |
| WO | 2010/107236 A2 | 9/2010 |
| WO | 2011/081253 A1 | 7/2011 |

OTHER PUBLICATIONS le Maire et al (Interaction of membrane proteins and lipids with solubilizing detergents, Biochimica et Biophysica Acta 1508 (2000) 86-111), Jan. 2000.*
Boland et al (Electrospinning polydioxanone for biomedical applications, Acta Biomaterialia 1 (2005) 115-123, Jan. 2005.*
International Preliminary Report on Patentability, dated Jan. 17, 2017 with an English translation of Written Opinion of the International Searching Authority of Oct. 13, 2015 for PCT/KR2015/007414.
International Search Report dated Oct. 13, 2015 for PCT/KR2015/007414, citing the above reference(s).
K. Garg et al., "Macrophage Functional Polarization (M1/M2) in Response to Varying Fiber and Pore Dimensions of Electrospun Scaffolds", Biomaterials., 27 pages, Jun. 2013.
Korean Office Action dated Dec. 19, 2014 in connection with the counterpart Korean Patent Application No. 10-2014-0090590, citing the above reference(s).
Grant of Patent from the Korean Intellectual Property Office dated Feb. 24, 2015 in connection with the counterpart Korean Patent Application No. 10-2014-0090590, citing the above reference(s).
Written Opinion of the International Searching Authority dated Oct. 13, 2015 for PCT/KR20151007414, citing the above reference(s).
Wang Tianqiang et al., "Regulation of shape and size of polymerized product of dioxanone in supercritical carbon dioxide", Sep. 24-28, 2011, p. 759, China Academic Journal Electronic Publishing House.

* cited by examiner

*Primary Examiner* — Gregory Listvoyb
(74) *Attorney, Agent, or Firm* — Hauptman Ham, LLP

(57) ABSTRACT

The present invention relates to a method for manufacturing polydioxanone particles (PDO) for a filler, more particularly to a method for manufacturing polydioxanone particles, which includes a step of mixing a solution of polydioxanone dissolved in a perfluoroalcohol with a polymer emulsion containing a polyethylene oxide-polypropylene oxide-polyethylene oxide terpolymer at a predetermined ratio to generate polydioxanone particles and then recovering the polydioxanone particles through aging and washing. The polydioxanone particles manufactured by the manufacturing method of the present invention can be favorably used as an injection for regenerating skin tissues.

10 Claims, 2 Drawing Sheets

[Fig. 1]
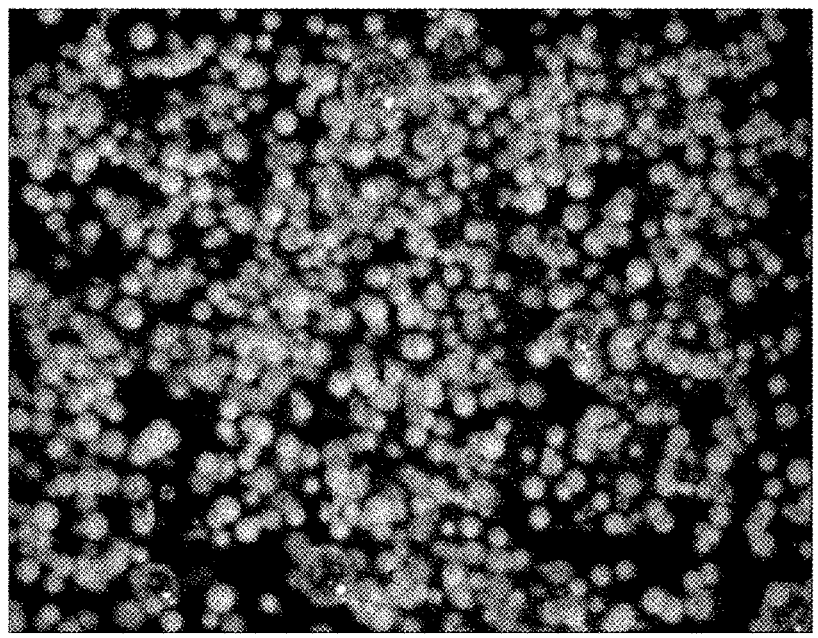

[Fig. 2]
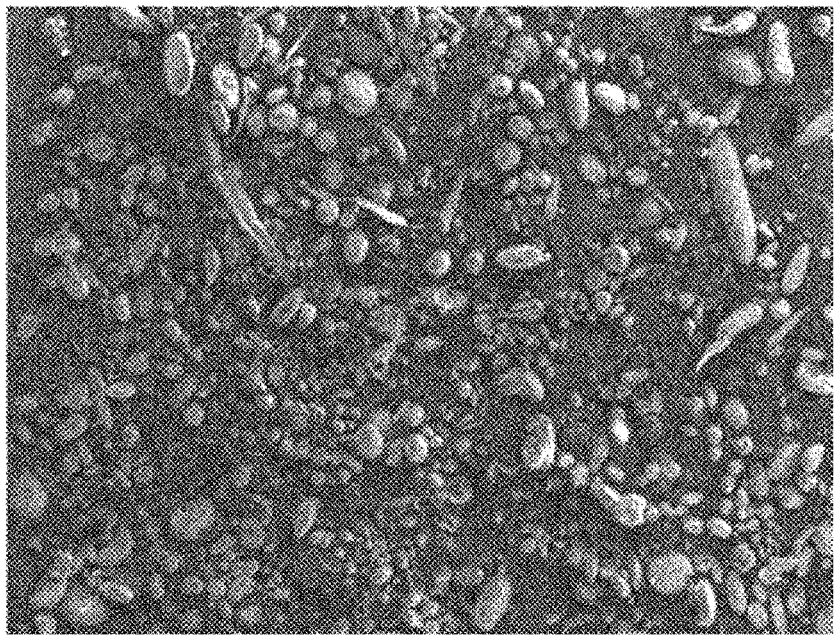
[Fig. 3]

METHOD FOR MANUFACTURING POLYDIOXANONE PARTICLES FOR FILLER

CROSS REFERENCE TO RELATED APPLICATION

This present application is a national stage filing under 35 U.S.C § 371 of PCT application number PCT/KR2015/007414 filed on Jul. 16, 2015 which is based upon and claims the benefit of priority to Korean Patent Application No. 10-2014-0090590 filed on Jul. 17, 2014 in the Korean Intellectual Property Office. The disclosures of the above-listed applications are hereby incorporated by reference herein in their entirety.

TECHNICAL FIELD

The present invention relates to a method for manufacturing polydioxanone particles for a filler, more particularly to a method for manufacturing polydioxanone particles, which includes a step of mixing a solution of polydioxanone dissolved in a perfluoroalcohol with a polymer emulsion containing a polyethylene oxide-polypropylene oxide-polyethylene oxide terpolymer in a predetermined ratio to generate polydioxanone particles and then recovering the polydioxanone particles through aging and washing.

BACKGROUND ART

Methods for manufacturing polymer particles largely include emulsion polymerization, dispersion polymerization, seed polymerization and suspension polymerization. Among them, the emulsion polymerization method is employed the most widely because it is easy to manufacture particles of a very uniform particle size distribution. However, the polymer particles manufactured by emulsion polymerization do not exceed 1 µm in diameter and a surfactant used to improve the stability of the particles tend to be adsorbed on the surface of the particles, thereby causing foaming or deterioration of physical properties.

In dispersion polymerization, ethanol, methanol, etc. may be used alone as a reaction medium, or another organic solvent such as toluene, benzene, 2-methoxyethanol, etc. or a small amount of water may be used together as a cosolvent. The size of the polymer particles manufactured by dispersion polymerization using such media is typically 1 µm or smaller. In addition, the dispersion polymerization method is disadvantageous in that particle size distribution varies very sensitively depending on the reaction environments such as the composition of reactants, presence of oxygen, etc. and process reproducibility is not good.

Seed polymerization is a method of manufacturing polymer particles with uniform particle size distribution of micrometer scales through swelling of monomers after dispersing particles of uniform size prepared through emulsion polymerization or dispersion polymerization in a dispersion medium. Although control of particle size is easy in seed polymerization, it is disadvantageous in that the polymerization process is very complicated and a long time is required because the polymerization is conducted in two or three steps.

Suspension polymerization is a method of manufacturing polymer particles from water-insoluble monomers using water as a dispersion medium in the presence of a steric stabilizer. However, because this method manufactures polymer particles by dispersing monomers in an aqueous solution by applying mechanical force, the obtained polymer particles have a very broad particle size distribution ranging from 0.1 to 1000 µm and an additional apparatus is necessary to reduce the particle size distribution. U.S. Pat. Nos. 4,017,670, 4,071,670, 4,085,169 and 4,129,706 and European Patent No. 0,443,609 disclose methods for manufacturing polymer particles with a final particle size of 5-50 µm by conducting suspension polymerization at a very high stirring speed of 10,000-30,000 rpm using three reactors connected serially or in parallel. U.S. Pat. No. 5,852,140 disclose a method for manufacturing polymer particles with a particle size of 0.1-5 µm by conducting bulk polymerization of monomers until a conversion rate reaches about 50% and then conducting second polymerization after dispersing the resulting oligomers in an aqueous solution in the presence of a dispersion medium using a high shear mixer.

However, because it is difficult to manufacture polymer particles with a uniform particle size through the suspension polymerization, Japanese Patent Publication No. H11-60615 and International Patent Publication No. WO99/19370 disclose a method of forming an aqueous solution of monomer droplets of relatively uniform particle size in the presence of a dispersing agent by employing the SPG (Shirasu porous glass) membrane emulsification technique and then producing polymer particles with a uniform diameter of 1-10 µm through suspension polymerization. However, this method requires an additional process of the membrane emulsification and is uneconomical because the expensive solvent 1,1,1,3,3,3-hexafluoro-2-propanol is used to manufacture polydioxanone (PDO) particles.

DISCLOSURE

Technical Problem

The present invention is directed to providing a method for manufacturing polydioxanone particles which are readily applicable to a living body and highly biocompatible and can improve skin's volume for several months by being injected into the living body.

The present invention is also directed to providing a use of the particles manufactured by the method as an injection for skin resurfacing or tissue reconstruction.

Technical Solution

In an aspect, the present invention provides a method for manufacturing polydioxanone particles for a filler, including:

a) a step of preparing a polydioxanone solution by dissolving polydioxanone in a perfluoroalcohol;

b) a step of preparing a polymer emulsion by mixing and stirring a polyethylene oxide-polypropylene oxide-polyethylene oxide terpolymer, an acid, water and a surfactant;

c) a step of generating polydioxanone particles by mixing the polymer emulsion with the polydioxanone solution and stirring the mixture;

d) a step of aging the polydioxanone particles by adding a stabilizer to the dispersion in which the particles are dispersed and stirring the same; and e) a step of recovering the polydioxanone particles and purifying them by washing.

In another aspect, the present invention provides an injection for skin resurfacing and tissue reconstruction, which contains the polydioxanone particles manufactured by the method.

Advantageous Effects

A manufacturing method of the present invention allows manufacturing polydioxanone particles of desired size by controlling the amount of a polyethylene oxide (PEO)-polypropylene oxide (PPO)-polyethylene oxide (PEO) terpolymer and an acid.

Because the process of the manufacturing method of the present invention is simpler than the existing methods for manufacturing polymer particles, it is advantageous in terms of initial cost and does not require an additional process. Furthermore, the polydioxanone particles can be manufactured in large scale in short time at low cost and with minimal use of an organic solvent due to the interaction between the acid, water and the terpolymer although polydioxanone has a relatively low solubility in the solvent.

The polydioxanone particles manufactured by the method of the present invention are readily applicable to a living body and highly biocompatible. When injected into the living body, they can improve skin's vitality and elasticity by activating the skin's dermal layer and thereby regenerating cells around the particles.

Because the polydioxanone particles manufactured by the method of the present invention can improve skin's volume for several months by being injected into the skin, they can be widely used as a filler.

BRIEF DESCRIPTION OF DRAWINGS

FIG. 1 shows an electron microscopic image (×100) of amorphous polydioxanone particles manufactured by a manufacturing method of the present invention.

FIG. 2 shows an electron microscopic image (×100) of amorphous polydioxanone particles manufactured by the existing seed polymerization method.

FIG. 3 shows an electron microscopic image of polydioxanone particles manufactured by the existing suspension polymerization method. It can be seen that particles were not formed.

BEST MODE FOR CARRYING OUT INVENTION

The present invention relates to a method for manufacturing polydioxanone particles which are readily applicable to a living body and provide a useful effect in tissue growth when injected into the living body and thus can be widely used in the field of tissue engineering.

Hereinafter, the individual steps of the method for manufacturing polydioxanone particles according to the present invention are described in detail.

The first step is a step wherein a polydioxanone solution is prepared.

That is to say, a polydioxanone solution is prepared by dissolving polydioxanone in a perfluoroalcohol. The polydioxanone (PDO) is a biocompatible and biodegradable polymer. As the polydioxanone, one having a weight-average molecular weight ranging from 200,000 to 250,000 is used.

A perfluoroalcohol is used as a solvent for dissolving the polydioxanone. As the perfluoroalcohol, a $C_1$-$C_6$ alcohol compound substituted with 3-13 fluorine atoms is used. For example, 1,1,1,3,3,3-hexafluoro-2-propanol may be used.

The concentration of the polydioxanone in the polydioxanone solution is maintained at 1.0-5.0 wt %. When the concentration exceeds the above limit, the polydioxanone particles may not be formed stably due to separation of aqueous and organic layers and the formed particles may have a nonuniform particle size.

The second step is a step wherein a polymer emulsion is prepared.

That is to say, a polymer emulsion is prepared by mixing and stirring a polyethylene oxide (PEO)-polypropylene oxide (PPO)-polyethylene oxide (PEO) terpolymer, an acid, water and a surfactant.

The PEO-PPO-PEO terpolymer serves as a stabilizer which allows the polydioxanone solution to be stably and uniformly dispersed in water. As the PEO-PPO-PEO terpolymer, one having a weight-average molecular weight of 1,000-50,000 g/mol, specifically 10,000-20,000 g/mol, is used. In the present invention, the PEO-PPO-PEO terpolymer is adsorbed on the surface of the polydioxanone and prevents interaction between the particles. That is to say, the PEO-PPO-PEO terpolymer acts as a bridge between the aqueous solution and the polydioxanone particles, thereby preventing aggregation and precipitation due to hydrophobic interaction of the dispersed polydioxanone particles. Specifically, the hydrophobic groups of the PEO-PPO-PEO terpolymer dispersed in the polydioxanone solution surround the polydioxanone dissolved in the solvent and perform a microemulsion to form an adsorbed film on the particles, thereby preventing the aggregation. Specifically, the PEO-PPO-PEO terpolymer may be contained in the polymer emulsion at a concentration of 0.1-2.0 wt %. When the concentration of the PEO-PPO-PEO terpolymer contained in the polymer emulsion is lower than 0.1 wt %, the polydioxanone particles may aggregate with each other without being uniformly dispersed in the solvent. And, when the concentration exceeds 2.0 wt %, the size and shape of the polydioxanone particles may not be maintained uniformly.

In the present invention, an acid is used in the process where the polymer emulsion is prepared. The acid aids in the formation of the polydioxanone particles in the presence of the PEO-PPO-PEO terpolymer. The acid may be one or more selected from a group consisting of hydrochloric acid, nitric acid, acetic acid, sulfuric acid, carbonic acid, phosphoric acid and boric acid and may be used as an aqueous solution by being dissolved in water at a concentration of 20-40 wt %. When the acid is used as a 40 wt % acid solution, it may be used in an amount of 0.5-3.5 parts by weight based on 100 parts by weight of the solution containing the PEO-PPO-PEO terpolymer. The acid may be used in such an amount that the pH of the polymer emulsion is 1.5-4.5. When the acid is used outside of the range, the size of the polydioxanone particles may be nonuniform or the particles may not be formed due to phase separation.

The water and the surfactant are used to form the emulsion. The water and the surfactant used to form the emulsion may be used at a weight ratio of specifically 1:0.001-1:0.02, more specifically 1:0.01-1:0.02. The surfactant may be any commonly used surfactant, including anionic, cationic or amphoteric surfactants. In the present invention, the commercially available Tween products may be used as the surfactant. For example, polyoxyethylene sorbitan monolaurate (Tween 20), polyoxyethylene sorbitan monopalmitate (Tween 40), polyoxyethylene sorbitan monostearate (Tween 60), polyoxyethylene sorbitan monooleate (Tween 80), polyoxyethylene sorbitan trioleate (Tween 85), etc. may be used.

The third step is a step wherein polydioxanone particles are formed.

That is to say, polydioxanone particles with an average particle diameter of 1-150 μm and a uniform particle size are prepared by mixing the polymer emulsion with the polydioxanone solution and stirring the mixture. During the stirring, the particles may be stabilized according to a method commonly used in the art, for example, using an ultrasonicator or a high-speed stirrer. The method for stabilizing the particles in the step of generating the polydioxanone particles is not particularly limited in the present invention.

The fourth step is a step wherein the generated polydioxanone particles are aged.

That is to say, the polydioxanone particles are aged by adding a stabilizer to the dispersion in which the particles are dispersed and stirring the same. In the present invention, the stabilizer is added so that the particles can be aged stably. The stabilizer may be one or more selected from a group consisting of a $C_1$-$C_4$ alcohol (e.g., methanol, ethanol, isopropanol or butanol), ethyl acetate, acetic acid, acetaldehyde, methylene chloride, chloroform, acetone, dimethylformamide and an aqueous solution thereof. In the examples of the present invention, ethanol or an aqueous ethanol solution are mainly used as the stabilizer. However, the stabilizer is never limited to them in the present invention. The stabilizer may be used in an amount of 100-500 parts by weight based on 100 parts by weight of the polymer emulsion. Outside this range, it is difficult to obtain polydioxanone particles of the size desired in the present invention.

The fifth step is a step wherein the polydioxanone particles are purified.

That is to say, the polydioxanone particles are recovered and then purified by washing with a solvent. The solvent used for the washing may be water or one or more selected from ethanol, isopropyl alcohol, diethyl ether, ethyl acetate and acetic acid. More specifically, a mixture solvent of water and ethanol may be used and washing may be conducted while varying a weight ratio of water:ethanol from 5:5 to 9:1.

Because the polydioxanone particles manufactured by the manufacturing method described above are readily applicable to a living body and highly biocompatible, they are useful as an injection for skin resurfacing and tissue reconstruction. When injected into the living body, the polydioxanone particles manufactured by the manufacturing method of the present invention can improve skin's vitality and elasticity by activating the skin's dermal layer and thereby regenerating cells around the particles. In addition, they can improve skin's volume for several months by being injected into the skin.

Accordingly, an injection for a filler containing the polydioxanone particles manufactured by the manufacturing method described above is also included in the scope of the present invention. The injection for a filler may further contain, in addition to the polydioxanone particles as an active ingredient, other filler additives commonly used for the purpose of cosmetic surgery. The filler additive that may be used in the present invention is one or more selected from a group consisting of hyaluronic acid, heparin, dextran, alginic acid, collagen, albumin, gelatin, chitosan, polytetrafluoroethylene, polyethylene, polyurethane, polyethylene glycol, polyglycol, polylactide, polyhydroxyvalerate, alginate and carboxymethyl cellulose. The filler additive may be used in an amount commonly used in the art and there is no particular limitation in the manufacturing method of the injection for a filler or the content of the filler additive in the present invention.

The present invention will be described in more detail through examples. The following examples are for illustrative purposes only and it will be apparent to those skilled in the art that the scope of this invention is not limited by the examples.

EXAMPLES

Example 1

A polydioxanone solution was prepared by dissolving 0.5 g of polydioxanone (PDO; weight-average molecular weight 200,000) in 50 g of 1,1,1,3,3,3-hexafluoro-2-propanol.

In a separate container, a polymer emulsion of pH 2.5 was prepared by stirring a mixture of 10 g of a polyethylene oxide (PEO)-polypropylene oxide (PPO)-polyethylene oxide (PEO) terpolymer (BASF, F127; weight-average molecular weight 12,600), 25 g of a 40% aqueous hydrochloric acid solution, 940 g of water and 0.1 g of Tween-80 as a surfactant.

A dispersion in which polydioxanone particles are uniformly dispersed was prepared by mixing the polydioxanone solution and the polymer emulsion and then high-speed stirring at 1500 rpm. After adding 1025 g of ethanol as a stabilizer to 1025 g of the dispersion, the particles were aged by stirring at 100 rpm. The aged polydioxanone particles were filtered, washed with water and then dried.

A result of measuring the size and physical properties of the manufactured polydioxanone particles is shown in Table 1.

Example 2. Properties of Polydioxanone Particles Manufactured with Polydioxanone Solutions of Different Concentrations Polydioxanone particles were manufactured in the same manner as in Example 1, except that the concentration of polydioxanone in the polydioxanone solution was varied to be 0.5, 1.0, 2.0, 3.0, 4.0, 5.0 and 5.5 wt %. The yield and size of the polydioxanone particles manufactured with the polydioxanone solutions of different concentrations are summarized in Table 1.

TABLE 1

| | | Concentration of PDO solution (wt %) | | | | | | |
|---|---|---|---|---|---|---|---|---|
| | | 0.5 | 1.0 | 2.0 | 3.0 | 4.0 | 5.0 | 5.5 |
| PDO particles | Particle size (μm) | x | 1-150 | 1-50 | 1-50 | 1-50 | 1-50 | x |
| | Yield (%) | — | 23 | 97 | 96 | 95 | 12 | — | x: Polydioxanone particles were not formed or particle aggregation occurred.

As seen from Table 1, polydioxanone particles could be formed when the concentration of the polydioxanone solution was 1-5 wt %. Specifically, polydioxanone particles with more uniform size could be manufactured when the concentration of the polydioxanone solution was 2-4 wt %.

Example 3. Properties of Polydioxanone Particles Manufactured with Polymer Emulsions Having Different Terpolymer Concentrations Polydioxanone particles were manufactured in the same manner as in Example 1, except that the content of the PEO-PPO-PEO terpolymer used in the preparation of the polymer emulsion was varied. That is to say, the concentration of the PEO-PPO-PEO terpolymer in the polymer emulsion was varied to be 0.05, 0.1, 0.5, 1.0, 1.5, 2.0 and 2.5 wt %. The yield and size of the polydioxanone particles manufactured with the polymer emulsions of different compositions are summarized in Table 2.

TABLE 2

| | | Concentration of PEO-PPO-PEO (wt %) | | | | | | |
|---|---|---|---|---|---|---|---|---|
| | | 0.05 | 0.1 | 0.5 | 1.0 | 1.5 | 2.0 | 2.5 |
| PDO particles | Particle size (μm) | x | 1-150 | 1-150 | 1-150 | 1-150 | 1-150 | x |
| | Yield (%) | — | 97 | 96 | 96 | 94 | 91 | — |

As seen from Table 2, polydioxanone particles could be formed when the concentration of the PEO-PPO-PEO terpolymer in the polymer emulsion was 0.1-2.0 wt %. When the concentration of the PEO-PPO-PEO terpolymer was 0.05 wt % or 2.5 wt %, polydioxanone particles were not formed or the particle size was not uniform.

Example 4. Properties of Polydioxanone Particles Manufactured with Polymer Emulsions Having Different Water and Surfactant Concentrations Polydioxanone particles were manufactured in the same manner as in Example 1, except that the weight ratio of the water and the surfactant used to prepare the polymer emulsion was varied. That is to say, the weight ratio of water/surfactant was varied to be 1/0, 1/0.001, 1/0.01, 1/0.02 and 1/0.1. The yield and size of the polydioxanone particles manufactured with the polymer emulsions of different compositions are summarized in Table 3.

TABLE 3

|  |  | Weight ratio of water/surfactant | | | |
|---|---|---|---|---|---|
|  |  | 1/0.001 | 1/0.01 | 1/0.02 | 1/0.1 |
| PDO particles | Particle size (μm) | 1-150 | 1-150 | 1-150 | x |
|  | Yield (%) | 75 | 98 | 95 | — |

As seen from Table 3, polydioxanone particles could be formed when the weight ratio of water/surfactant in the polymer emulsion was 1/0.001-1/0.02 weight ratio. In contrast, polydioxanone particles were not formed when the weight ratio of water/surfactant in the polymer emulsion was 1/0.1.

Example 5. Properties of Polydioxanone Particles Manufactured with Polymer Emulsions Having Different Amounts of Hydrochloric Acid Added Polydioxanone particles were manufactured in the same manner as in Example 1, except that the addition amount of the aqueous hydrochloric acid solution added when preparing the polymer emulsion was varied. That is to say, the pH of the polymer emulsion was adjusted by adding different amounts of the 40 wt % aqueous hydrochloric acid solution. The yield and size of the polydioxanone particles manufactured with the polymer emulsions of different pH are summarized in Table 4.

TABLE 4

|  |  | pH of polymer emulsion | | | | | |
|---|---|---|---|---|---|---|---|
|  |  | ≤1.0 | 1.5 | 2.5 | 3.5 | 4.5 | ≥5.0 |
| PDO particles | Particle form | Amorphous | Amorphous | Amorphous | Amorphous | Amorphous | Amorphous |
|  | Particle size (μm) | ≤1 | 18 ± 10 | 51 ± 10 | 84 ± 10 | 139 ± 10 | ≥150 |
|  | Yield (%) | — | 97 | 96 | 98 | 98 | — |

As seen from Table 4, an average particle size of 1-150 μm could be maintained when the pH of the polymer emulsion was 1.5-4.5. The particle size tended to increase as the pH of the polymer emulsion increased. At pH<1.0, particles were not formed or fine particles smaller than 1 μm were formed. At pH>5.0, large particles of 150 μm or greater were formed.

Comparative Example 1

Polydioxanone (PDO) Particles were Manufactured by Seed Polymerization.

That is to say, polydioxanone (PDO) particles with a uniform particle size distribution in micrometer scale were manufactured by dispersing polydioxanone seed particles in 1,1,1,3,3,3-hexafluoro-2-propanol as a dispersion medium and swelling monomers.

Comparative Example 2

Polydioxanone (PDO) Particles were Manufactured by Suspension Polymerization.

Suspension polymerization is a method of manufacturing polydioxanone (PDO) particles using water-insoluble monomers in water as a dispersion medium in the presence of a steric stabilizer. However, because the suspension polymerization method manufactures the particles by dispersing the monomers in an aqueous solution by applying mechanical force, the obtained polymer particles have a very nonuniform size or particles are not formed due to remarkably decreased solubility of polydioxanone (PDO), as shown in FIG. 3.

TABLE 5

|  |  | Example 1 | Comparative Example 1 | Comparative Example 2 |
|---|---|---|---|---|
| PDO particles | Particle form | Amorphous | Amorphous | Not formed |
|  | Particle size (μm) | 1-150 | 0.1-1500 | x |
|  | Yield (%) | 96 | 42 | — |

FIGS. 1-3 show the electron microscopic images of the polydioxanone particles manufactured according to the present invention in Example 1 (FIG. 1), the polydioxanone particles manufactured by seed polymerization in Comparative Example 1 (FIG. 2) and the polydioxanone particles manufactured by suspension polymerization in Comparative Example 2 (FIG. 3).

From FIG. 1, it can be seen that the polydioxanone particles manufactured in Example 1 are uniform in size and shape. In contrast, although the polydioxanone particles manufactured by seed polymerization (FIG. 2) were amorphous, the size was very nonuniform. And, polydioxanone particles were not formed by the suspension polymerization method due to aggregation (FIG. 3).

Test Example 1. Comparison of Properties of PDO Raw Material and PDO Particles

The physical and chemical properties of the polydioxanone raw material and the polydioxanone particles manufactured by the method of the present invention using the raw material were compared as follows.

[Test Method]

1) Inherent viscosity (IV) was measured using a high-frequency viscometer for smallest sample volumes. First, after taking samples (0.1 g) r and then dissolving them in a 1,1,1,3,3,3-hexafluoro-2-propanol (HFIP) solvent at a concentration of 0.1% (w/v) at 30° C., 5 mg of each sample was subjected to the measurement.

2) Glass transition temperature ($T_g$) and melting point ($T_m$) were measured by differential scanning calorimetry (DSC) while raising temperature from −20° C. to 150° C. at a rate of 1° C./min.

3) Average molecular weight was measured by THF-GPC. Poly(methyl methacrylate) (PMMA) in a 1,1,1,3,3,3-hexafluoro-2-propanol (HFIP) eluent was used as a reference material and the measurement was made at room temperature (25±1° C.).

TABLE 6

|  | PDO pellets | PDO particles |
|---|---|---|
| Inherent viscosity (dL/g) | 1.8 ± 3 | 1.7 ± 1 |
| $T_g$ (° C.) | −7 ± 2 | −8 ± 1 |
| $T_m$ (° C.) | 112 ± 2 | 112 ± 1 |
| Average molecular weight (g/mol) | 230,000 ± 20,000 | 210,000 ± 10,000 |

PDO pellets: PDO raw material used in Example 1
PDO particles: PDO particles manufactured in Example 1 using PDO raw material As seen from Table 6, no distinct difference could be found in the intrinsic viscosity, glass transition temperature, melting point or average molecular weight. Accordingly, it can be seen that the method of the present invention causes little difference in the physical and chemical properties of the polydioxanone.

INDUSTRIAL APPLICABILITY

As described above, polydioxanone is a biodegradable and biocompatible material and the polydioxanone (PDO) particles manufactured by the manufacturing method of the present invention can be usefully used as an injection for regenerating skin tissues.

The invention claimed is:

1. A method for manufacturing polydioxanone particles for a filler, the method comprising:
preparing a polydioxanone solution by dissolving polydioxanone in a perfluoroalcohol;
preparing a polymer emulsion by mixing and stirring a polyethylene oxide-polypropylene oxide-polyethylene oxide terpolymer, an acid, water and a surfactant;
generating polydioxanone particles by mixing the polymer emulsion with the polydioxanone solution and stirring the mixture;
aging the polydioxanone particles by adding a stabilizer to the dispersion in which the particles are dispersed and stirring the same; and
recovering the polydioxanone particles and purifying them by washing,
wherein the weight ratio of the surfactant to the water is 0.001 to 0.02,
wherein the concentration of the polyethylene oxide-polypropylene oxide-polyethylene oxide terpolymer in the polymer emulsion is 0.1 wt % to 2.0 wt %, and
wherein the acid is used in an amount that the pH of the polymer emulsion is 1.5-4.5.

2. The method according to claim 1, wherein the perfluoroalcohol is a $C_1$-$C_6$ alcohol compound substituted with 3-13 fluorine atoms.

3. The method according to claim 2, wherein the perfluoroalcohol is 1,1,1,3,3,3-hexafluoro-2-propanol.

4. The method according to claim 1, wherein the concentration of the polydioxanone in the polydioxanone solution is 1.0 wt % to 5.0 wt %.

5. The method according to claim 1, wherein the polyethylene oxide-polypropylene oxide-polyethylene oxide terpolymer has a weight-average molecular weight of 1,000 g/mol to 50,000 g/mol.

6. The method according to claim 1, wherein the acid is selected from a group consisting of hydrochloric acid, nitric acid, acetic acid, sulfuric acid, carbonic acid, phosphoric acid and boric acid and is used as an aqueous solution by being dissolved in the water at a concentration of 20 wt % to 40 wt %.

7. The method according to claim 1, wherein the surfactant in b) is one or more selected from a group consisting of polyoxyethylene sorbitan monolaurate, polyoxyethylene sorbitan monopalmitate, polyoxyethylene sorbitan monostearate, polyoxyethylene sorbitan monooleate and polyoxyethylene sorbitan trioleate.

8. The method according to claim 1, wherein the stirring is performed using an ultrasonicator or a high-speed stirrer.

9. The method according to claim 1, wherein the stabilizer is selected from a group consisting of methanol, ethanol, isopropanol, butanol, ethyl acetate, acetic acid, acetaldehyde, methylene chloride, chloroform, acetone, dimethylformamide and an aqueous solution thereof.

10. The method according to claim 1, wherein the stabilizer is used in an amount of 100 parts by weight to 500 parts by weight based on 100 parts by weight of the polymer emulsion.

* * * * *